BEST AVAILABLE COPY

J. J JOHNSTON.

Assignor, by mesne assignments, to THE AMERICAN HYDROCARBON GAS CO.

Apparatus for Evaporating Liquids.

No. 8,373. Reissued Aug. 13, 1878.

Witnesses.
T. E. O'Brien
Wm Blackstock Jr.

Inventor.
James J. Johnston
By Hill Sherman
His attorneys.

2 Sheets—Sheet 2

J. J JOHNSTON.

Assignor, by mesne assignments, to THE AMERICAN HYDROCARBON GAS CO.

Apparatus for Evaporating Liquids.

No. 8,373. Reissued Aug. 13, 1878.

Witnesses.
T. E. O'Brien
Wm Blackstock Jr.

Inventor
James J. Johnston
By Hill Blewett
His Attorneys.

UNITED STATES PATENT OFFICE.

JAMES J. JOHNSTON, OF COLUMBIANA, OHIO, ASSIGNOR, BY MESNE ASSIGNMENTS, TO THE AMERICAN HYDROCARBON GAS COMPANY, OF PITTSBURG, PENNSYLVANIA.

IMPROVEMENT IN APPARATUS FOR EVAPORATING LIQUIDS.

Specification forming part of Letters Patent No. 50,935, dated November 14, 1865; antedated November 2, 1865; Reissue No. 5,570, dated September 9, 1873; Reissue No. 8,272, dated August 13, 1878; application filed January 25, 1878.

DIVISION A.

*To all whom it may concern:*

Be it known that I, JAMES J. JOHNSTON, of Columbiana, in the county of Columbiana and State of Ohio, have invented a certain new and Improved Apparatus for Evaporating Liquids; and I do hereby declare the following to be a full and exact description of the same, reference being had to the accompanying drawings, forming part of this specification, in which—

Figure 1:
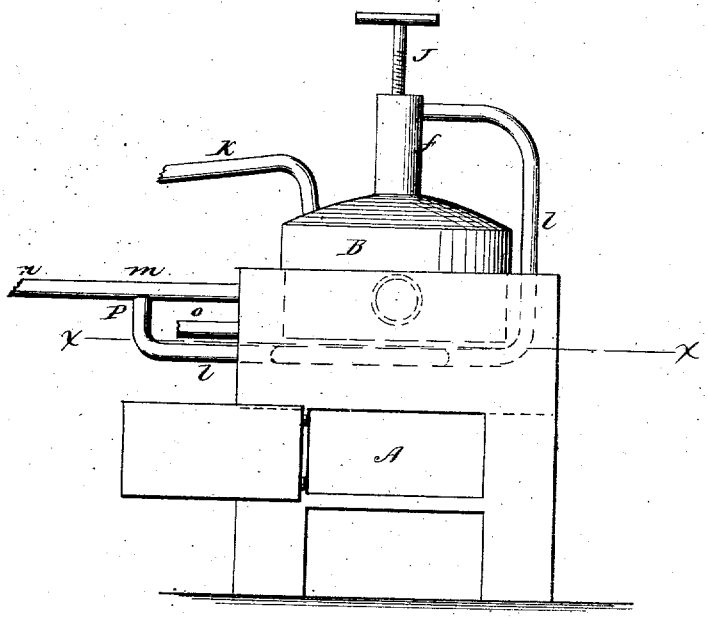
Figure 2:
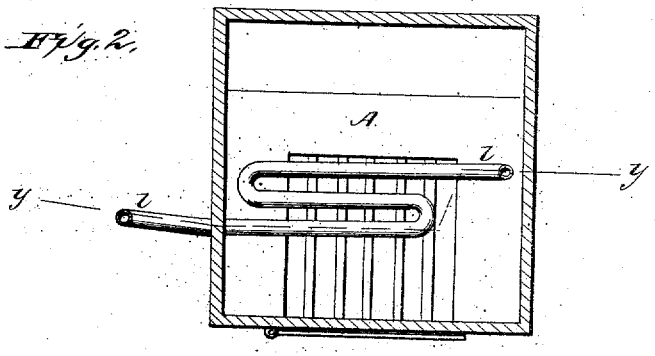
Figure 3:
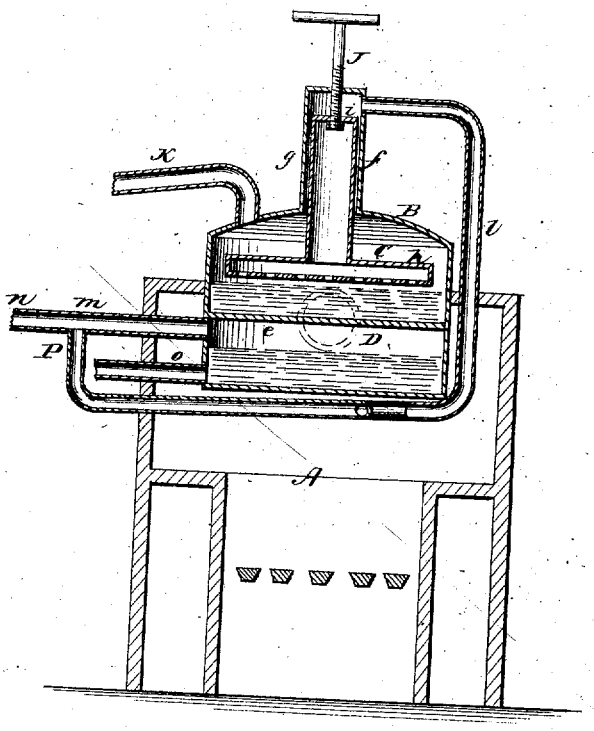

Figure 1 is a front elevation; Fig. 2, a horizontal section in line *x x* of Fig. 1; and Fig. 3, a vertical section in line *y y* of Fig. 2.

Similar letters of reference in the several figures denote the same parts.

The nature of this part of my invention consists in an improved apparatus for evaporating and vaporizing liquids; and the invention, so far as herein claimed, consists in the combination of a chamber for evaporating and vaporizing the liquids with means for superheating air and steam and mingling them with the vapors of the liquid while all are in a highly-heated condition, the process of producing a useful product from hydrocarbon liquids by means of the apparatus being claimed in another division of this application.

In the drawings, A represents the furnace, and B represents the still or retort, which is divided into two compartments, C D, by means of a partition, *e*. The compartment C is furnished with a hollow column, *f*, into the bore of which is fitted another column, *g*, on the lower end of which is a disk, *h*, the lower face of which is perforated with a large number of small openings, and in the upper end of the column *g* are a number of openings, *i*.

The column *g* and its disk *h* are suspended in the column *f* and still C by means of a screw, J, whereby they can be raised and lowered in the still, so that the disk may be just above the liquid therein or lowered below its surface to any desired point. To the crown of the still or retort is fixed a pipe, *k*, for the purpose of carrying off the vapor evolved from the liquid in the still. To the upper end of the column *f* is attached a pipe, *l*, which passes down into the furnace A, and traversing back and forth under the still passes out of the furnace, and is connected to the pipe *m* communicating with the upper portion of the compartment D of the still or retort. Near the bottom of the compartment D is a pipe, *o*, communicating with a water-supply. To the branch *n* of the pipe *m* should be attached an air-blast device.

From the foregoing description, and by reference to the accompanying drawings, the skillful mechanic will readily understand the construction and arrangement of the device herein shown and described for evaporating and vaporizing liquids; but I wish it clearly understood that I do not confine myself to the particular construction of the several parts, as they may be varied without departing from the principle of the invention.

The compartment A being supplied with water, and the compartment C with the oil or other liquid to be evaporated and vaporized, fire is made in the furnace, which will generate steam in the compartment D, which will heat the liquid in the compartment C, and as soon as a sufficient pressure of steam is generated it will pass through the pipe *m*, and, the air-blast device being put in operation, the steam and air will combine at the point P, and entering the pipe *l* will pass through it and enter the column *f*, and pass through the openings *i* into the column *g*, and down into the disk *h*, and out through the small openings therein, and, acting on the surface of the heated liquid, will rapidly evaporate and vaporize it, and the air and steam, combined and superheated, having performed their office on or in the liquid in the compartment C, will commingle with the vapor and pass off through the pipe *k* to the condenser or elsewhere. The branch *n* of the pipe *m* may communicate with a steam-engine for the purpose of operating it.

The apparatus herein described is of great utility for vaporizing all liquids where the presence of air and steam are not objectionable, and it is especially useful in the treatment of hydrocarbon liquids where it is desirable to obtain an intimate combination of air and steam with their vapors.

Having thus described my invention, what I claim herein is—

1. The combination of a vaporizing-chamber, a steam and air superheater communicating therewith, and means for commingling the vapor, steam, and air in a highly-heated condition, substantially as described.

2. The combination of the furnace A, still B, adjustable disk *h*, and pipes *k*, *l*, and *m*, substantially as herein described, and for the purpose set forth.

JAMES J. JOHNSTON.

Witnesses:
WM. BLACKSTOCK,
MELVILLE CHURCH.